United States Patent

Marquais-Bienewald et al.

(10) Patent No.: US 8,118,883 B2
(45) Date of Patent: Feb. 21, 2012

(54) POLYMERIC HAIR DYES

(75) Inventors: Sophie Marquais-Bienewald, Hegenheim (FR); Christian Cremer, Lörrach (DE); Olof Wallquist, Bottmingen (CH); Robert Hochberg, Merzhausen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/812,785

(22) PCT Filed: Jan. 7, 2009

(86) PCT No.: PCT/EP2009/050087
§ 371 (c)(1),
(2), (4) Date: Dec. 1, 2010

(87) PCT Pub. No.: WO2009/090121
PCT Pub. Date: Jul. 23, 2009

(65) Prior Publication Data
US 2011/0088173 A1     Apr. 21, 2011

(30) Foreign Application Priority Data
Jan. 17, 2008 (EP) .................................. 08150355

(51) Int. Cl.
*A61Q 5/10* (2006.01)
*C07D 213/09* (2006.01)
(52) U.S. Cl. .......... 8/405; 8/552; 8/554; 8/647; 546/253
(58) Field of Classification Search .............. 8/405, 552, 8/554, 647; 546/253
See application file for complete search history.

(56) References Cited

U.S. PATENT DOCUMENTS

| | | | |
|---|---|---|---|
| 4,182,612 A | 1/1980 | Sokol | |
| 4,228,259 A | 10/1980 | Kalopissis | |
| 5,705,605 A | 1/1998 | Tittmann | |
| 6,306,182 B1 | 10/2001 | Chan | |
| 7,731,761 B2 | 6/2010 | Marquais-Bienewald | |

FOREIGN PATENT DOCUMENTS

| | | |
|---|---|---|
| DE | 1469825 A1 | 1/1969 |
| FR | 2456764 A2 | 12/1980 |
| GB | 946472 A | 1/1964 |
| WO | 9501772 A1 | 1/1995 |
| WO | 01/17356 A1 | 3/2001 |
| WO | WO 2008/009579 A1 * | 1/2008 |

OTHER PUBLICATIONS

STIC Search Report dated Mar. 18, 2011.*
Translation of FR 2456764 Printed on Oct. 11, 2010.
Copending U.S. Appl. No. 12/812,782, filed Jul. 14, 2010.
Copending U.S. Appl. No. 12/812,781, filed Jul. 14, 2010.
Copending U.S. Appl. No. 12/812,778, filed Jul. 14, 2010.

* cited by examiner

*Primary Examiner* — Eisa Elhilo
(74) *Attorney, Agent, or Firm* — Shiela A. Loggins

(57) ABSTRACT

Disclosed are polymeric dyes obtained by the reaction of (a) a basic polycondensate with (b) an electrophilic dye of formula (2) $P-X-Y^{a+} An^{a+}$; wherein the basic polycondensate (a) is obtained by the reaction of ($a_1$) an amine of formula (I) in the presence of an anhydrous solvent with an ammonium salt ($a_2$) with a cyanamide:

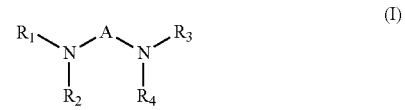

(I)

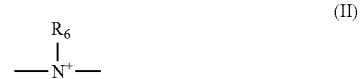

(II)

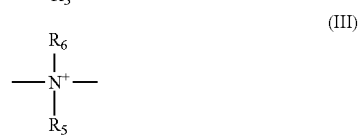

(III)

Wherein P, X, Y, a+, a, $a_1$, $a_2$, An, $R_1$, $R_2$, $R_3$, $R_4$, $R_5$, $R_6$ and A are defined in the claims and in the disclosure. The present invention also relates to compositions comprising these polymeric dyes, to a process for their use for dyeing of organic materials, such as keratin fibers, wool, leather, silk, cellulose or polyamides.

18 Claims, No Drawings

POLYMERIC HAIR DYES

The present invention relates to novel polymeric dyes and compositions comprising these compounds, to a process for their preparation and to their use for dyeing of organic materials, such as keratin-containing fibers, wool, leather, silk, cellulose or polyamides.

It is well known that cationic compounds have a good affinity to negative charged hair. These characteristics have been used to contact the hair with small molecules, but also with polymers.

Numerous cationic polymeric dyes have been disclosed for use as a colorant for human hair, for example in U.S. Pat. No. 4,228,259; U.S. Pat. No. 4,182,612 or FR 2 456 764. These references teach that the polymer moiety has the cationic charge.

Surprisingly it was found that very good dyeing results are obtained with polymeric hair dyes wherein the cationic charge is located in dye moiety.

Therefore the present invention relates to polymeric dyes obtained by the reaction of
(a) a basic polycondensate with
(b) an electrophilic dye of formula
(2) $P-X-Y^{a+} An^{a-}$; wherein
the basic polycondensate (a) is obtained by the reaction of
($a_1$) an amine of formula

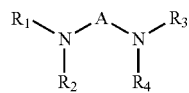

in the presence of an anhydrous solvent with an ammonium salt
($a_2$) with a cyanamide;
wherein
$R_1$, $R_2$, $R_3$ and $R_4$ independently from each other are hydrogen; or $C_1$-$C_4$alkyl, which may be substituted by amino, hydroxy, cyano or $C_1$-$C_4$alkoxy;
A is $C_2$-$C_{20}$alkylene, which may be substituted or interrupted by one or more than one hetero atoms;
P is a reactive grouping capable of reacting with a nitrogen nucleophile;
X is a linkage group selected from $C_1$-$C_{30}$alkylene, $C_2$-$C_{12}$alkenylene, $C_5$-$C_{10}$arylene, $C_5$-$C_{10}$cycloalkylene and $C_1$-$C_{10}$alkylene($C_5$-$C_{10}$arylene) which may be interrupted and/or terminated at one or both ends by one or more than one —O—, —S—, —N=, —N($R_5$)—, —S(O)—, SO$_2$, —(CH$_2$CH$_2$—O)$_{1-5}$—, —(CH$_2$CH$_2$CH$_2$—O)$_{1-5}$—, —C(O)—, —C(O)O—, —OC(O)—,

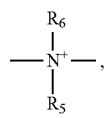

—CON($R_5$)—, —C(NR$_5$R$_6$)$_2$—, —($R_5$)NC(O)—, —C(S)$R_5$— or an optionally substituted, saturated or unsaturated, fused or non-fused aromatic or nonaromatic (hetero)cyclic bivalent radical optionally comprising at least one heteroatom; —O—; —S—; —N($R_5$)—; —S(O)—; —SO$_2$—; —(CH$_2$CH$_2$—O)$_{1-5}$—; —C(O)—; —C(O)O—; —OC(O)—;

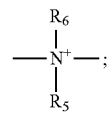

—CON($R_5$)—; —SO$_2$N($R_5$)—; —C(NR$_5$R$_6$)$_2$—; —($R_5$)NC(O)—; —C(S)$R_5$—; saturated or unsaturated, fused or non-fused aromatic or nonaromatic bivalent radical optionally comprising at least one heteroatom; which is optionally substituted by $C_1$-$C_{30}$alkyl, $C_1$-$C_{30}$alkoxy, $C_2$-$C_{12}$alkenyl, $C_5$-$C_{10}$aryl, $C_5$-$C_{10}$cycloalkyl, $C_1$-$C_{10}$alkyl($C_5$-$C_{10}$arylene), halogen or hydroxy; or the direct bond;
Y is a residue of an organic dye;
$R_5$ and $R_6$ independently from each other are hydrogen; unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl);
a is 1, 2 or 3; and
An is an anion.

$C_1$-$C_{14}$alkyl is for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl, n-hexyl, n-octyl, 1,1',3,3'-tetramethylbutyl or 2-ethylhexyl, nonyl, decyl, undecyl, dodecyl, tridecyl or tetradecyl.

$C_2$-$C_{14}$alkenyl is for example allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl or n-octadec-4-enyl.

$C_6$-$C_{10}$aryl is for example phenyl or naphthyl.

$C_1$-$C_{30}$alkylene is for example methylene, ethylene, propylene, isopropylene, n-tetramethylene, sec-tetramethylene, tert-tetramethylene, n-pentamethylene, 2-pentamethylene 3-penta-methylene, 2,2'-dimethylpropylene, cyclopentamethylene, cyclohexamethylene, n-hexamethylene, n-octamethylene, 1,1',3,3'-tetramethyltetramethylene, 2-ethylhexamethylene, nonamethylene, decamethylene, tridecamethylene, tetradecamethylene, pentadecamethylene, hexadecamethylene, heptadecamethylene, octadecamethylene, nonadecamethylene or eicosamethylene.

X is preferably a bivalent radical of formula (1a) -(T)$_t$(Z)$_z$—, wherein
T is a radical selected from saturated or unsaturated, linear or branched —$C_1$-$C_{12}$alkylene, —C(O)—, —(CH$_2$CH$_2$—O)$_{1-5}$—, —(CH$_2$CH$_2$CH$_2$—O)$_{1-5}$—, —C(O)O—, —OC(O)—, —N($R_5$)—, —CON($R_5$)—, —($R_5$)NC(O)—, —O—, —S—, —S(O)—, —S(O)$_2$—, —S(O)$_2$N($R_5$)— and —N$^+$($R_5$)($R_6$)—, which may be interrupted and/or terminated at one or both ends by one or more than one —O—, —S—, —N($R_5$)—, —C(O)—,

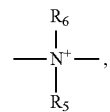

—CON($R_5$)—, —($R_5$)NC(O)— and which is optionally substituted by $C_1$-$C_6$alkyl, $C_1$-$C_6$alkoxy, $C_6$-$C_{10}$aryl, halogen or hydroxy;
Z is —(CH$_2$)$_2$SO$_2$—; —CH$_2$—CHR$_6$—CO—NR$_5$—; or a biradical of formula (1b)

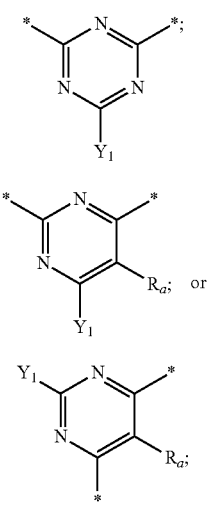

R$_5$ and R$_6$ independently from each other are hydrogen; C$_1$-C$_6$alkyl; C$_1$-C$_6$-alkoxy; C$_1$-C$_6$-alkylamino; C$_6$-C$_{10}$aryloxy; or C$_6$-C$_{10}$arylamino;

R$_a$ is hydrogen; C$_1$-C$_6$alkyl; C$_1$-C$_6$-alkoxy; C$_1$-C$_6$-alkylamino; C$_6$-C$_{10}$-aryloxy; C$_6$-C$_{10}$-aryl-amino; SO$_2$R$_5$; chlorine; or fluorine;

Y$_1$ is R$_a$; or the residue of an organic dye;

a is 1, 2 or 3; and t and z, independently from each other are 0; or 1.

Y is preferably selected from the group of anthraquinone, acridine, azo, azamethine, hydra-zomethine, triphenylmethane, benzodifuranone, coumarine, diketopyrrolopyrrol, dioxazine, diphenylmethane, formazane, indigoid indophenol, naphthalimide, naphthoquinone, nitroaryl, merocyanine, methine oxazine, perinone, perylene, pyrenequinone, phtalocyanine, phenazine, quinoneimine, quinacridone, quinophtalone, styryl, stilbene, xanthene, thiazine and thioxanthene dyes.

More preferably, Y is selected from anthraquinone, azo, azomethine, hydrazomethine, merocyanine, methine and styryl dyes.

P is preferably selected from a halogen; tosylate; mesylate; sulfonylchloride; acid chloride; and another reactive grouping selected from an epoxide; and a Michael system selected from an α-β unsaturated carbonyl and a sulfonyl system.

Preferably the molecular weight of the polymeric dye is from 400 to 50000.

In formula (1)

A is preferably C$_1$-C$_{20}$alkylene.

"Anion" denotes, for example, an organic or inorganic anion, such as halide, preferably chloride and fluoride, sulfate, hydrogen sulfate, phosphate, boron tetrafluoride, carbonate, bicarbonate, oxalate or C$_1$-C$_8$alkyl sulfate, especially methyl sulfate or ethyl sulfate; anion also denotes lactate, formate, acetate, propionate or a complex anion, such as the zinc chloride double salt.

The polycondensate obtained in the reaction steps (a$_1$) and (a$_2$) are prepared according to a manner known per se, for example U.S. Pat. No. 5,705,605.

Illustrative examples of compounds of formula (1) which may suitably be used in reaction step (a) are typically 1,4-butanediamine, 1,6-hexanediamine, dipropylenetriamine, N-(2-aminoethyl)-1,3-propanediamine, N,N-bis(2-aminopropyl)methylamine, polyethylenimines or poly-ethylenepolyamines such as diethylenetriamine, triethylenetetramine, tetraethylenepentamine or pentamethylenehexamine.

The compound of formula (1) is preferably a polyethylenepolyamine, and most preferably diethylenetriamine or 1,6-hexanediamine.

Ammonium salts suitable for the preparation of the polymeric dyes according to the present invention are typically ammonium salts of organic or inorganic acids such as ammonium chloride, ammonium sulfate, ammonium carbonate, ammonium formate or ammonium acetate. The use of ammonium chloride is preferred.

The anhydrous solvent is typically a hydroxyl group-containing solvent, preferably one having a boiling point of above 150° C. and, more particularly, of above 180° C., or a mixture of different solvents of this kind.

Typical examples are ethylene glycol, 1,2- or 1,3-propylene glycol, butylene glycol, di-, tri- or tetraethylene glycol and the ethers thereof, as well as polyethylene glycols having a molecular weight from typically 600 to 5000, and mixtures thereof.

Cyanamides suitable for step (a$_2$) are typically cyanamide, dicyandiamide, guanidine and biguanidine. In step (a$_2$) the use of dicyandiamide or sodium dicyanamide is preferred.

In step (a$_1$) the compound of formula (1) and the ammonium salt are typically used in a molar ratio from 1:0.1 to 1:2.5, preferably from 1:0.7 to 1:2 and, most preferably, from 1:1 to 1:1.5. The amount of hydroxyl group-containing solvent may vary over a wide range and is typically from 0.2 to 20 mol and, preferably, from 0.4 to 5 mol per mol of the compound of formula (1).

The reaction step (a$_1$) is preferably carried out at elevated temperature, conveniently in the range from 80 to 200° C., preferably from 100 to 160° C. and, most preferably, from 110 to 140° C.

The compound of formula (1) is preferably charged to the hydroxyl group-containing solvent or solvent mixture, and the ammonium compound is then added to this mixture, in which case it is convenient to carry out the reaction step under inert conditions, typically under nitrogen.

The protonised compound of formula (1) obtained according to (a$_1$) is then reacted with e.g. 0.5 to 2 mol, preferably 0.8 to 1.5 mol, of cyanamide per mol of starting compound of formula (1).

The reaction according to (a$_2$) is preferably carried out in the presence of one or more than one of the above-mentioned hydroxyl group-containing solvents at elevated temperature, which may typically be in the range from 80-250° C. and, preferably, from 140 to 220° C.

The reaction products obtained in (a$_1$) and (a$_2$) are solid melts at room temperature having basic properties and forming clear solutions in water; they may be converted into their water-soluble salts by neutralization with inorganic or organic acids such as hydrochloric acid or acetic acid.

In reaction step (b) the aqueous solutions obtained in reaction steps (a$_1$) and (a$_2$) are reacted with the dyes of formula (2).

The reaction may be carried out in solvents like water, alcohols, like methanol, ethanol, 2-propanol or butanol; nitriles, like acetonitrile or propionitrile; amides, like dimethylformamides, dimethylacetamide, N-methylpyrolidone; chlorinated hydrocarbons like chloroform, chlorbrenzene or trichloroethylene; or other solvents like dimethylsulfoxide.

Customary, the reaction temperature is in the range of 0 to 150° C., preferably 20 to 110° C. during the mixing of the starting compounds.

The reaction time is generally dependent on the reactivity of the starting compounds, on the selected reaction temperature and on the desired conversion. The selected reaction time is usually in the range from three hours to seven days.

The selected reaction pressure is generally in the range from 0.1 to 10 bar especially from 0.2 to 3.0 bar and is more especially atmospheric pressure.

It may by desirable to conduct the reaction of compounds in the presence of a catalyst. Suitable catalysts are for example an alkali metal $C_1$-$C_6$alkyloxide, such as sodium-, potassium or lithium $C_1$-$C_6$alkyloxide, preferably sodium methoxide, potassium methoxide or lithium methoxide, or sodium ethoxide, potassium ethoxide or lithium ethoxide; or secondary or tertiary amines, for example, such as chinuclidine, piperidine, N-methylpiperidine, pyridine, trimethylamine, dimethylamine, diethylamine, triethylamine, trioctylamine, 1,4-diazabicyclo-[2.2.2]octan, chinuclidine, N-methylpiperidine; or alkalimetal acetate, for example such as sodium acetate, potassium acetate, or lithium acetate.

The molar ratio of the dye of formula (2) to the amine of formula (1) is generally selected in the range from 0, 1:1 to 3:5, especially in the range from 0, 5:1 to 2:1.

The product prepared according to the process of the present invention may be advantageously worked up and isolated, and if desired be purified.

Customary, the work up starts by decreasing the temperature of the reaction mixture in the range from 5 to 80° C., especially in the range from 20 to 50° C.

It may be advantageous to decrease the temperature slowly, over a period of several hours.

In general, the reaction product is usually filtered off and then washed with water, a solvent or a salt solution and subsequently dried.

Filtration is normally carried out in standard filtering equipment, for example Büchner funnels, filter presses, pressurised suction filters, preferably in vacuo.

The temperature for the drying is dependent on the applied pressure. Drying is usually carried out in vacuo at 50-200 mbar. The drying is usually carried out at a temperature in the range from 40 to 90° C.

Advantageously the product is purified by recrystallisation after isolation. Organic solvents and solvent mixtures are suitable for the recrystallisation.

The polymeric dyes according to the present invention are suitable for dyeing organic materials, such as keratin-containing fibers, wool, leather, silk, cellulose or polyamides, cotton or nylon, and preferably human hair including body hairs like eyebrows, eyelashes, pubic-, breast-, armpit- and beard hair.

Also animal hair can be colored with the dyes according to the present invention. The dyeings obtained are distinguished by their depth of shade and their good fastness properties to washing, such as, for example, fastness to light, shampooing and rubbing.

Generally, hair dyeing agents on a synthetic base may be classified into three groups:
 temporary dyeing agents
 semipermanent dyeing agents, and
 permanent dyeing agents.

The multiplicity of shades of the dyes can be increased by combination with other dyes.

Therefore the dyes of the present invention may be combined with dyes of the same or other classes of dyes, especially with direct dyes, oxidation dyes; dye precursor combinations of a coupler compound as well as a diazotized compound, or a capped diazotized compound; and/or cationic reactive dyes.

Direct dyes are of natural origin or may be prepared synthetically. They are uncharged, cationic or anionic, such as acid dyes.

The polymeric dyes of the present invention may be used in combination with at least one single direct dye different from the dyes of the present invention.

Examples of direct dyes are described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, and in "Europäisches Inventar der Kosmetikrohstoffe", 1996, published by The European Commission, obtainable in diskette form from the Bundesver-band der deutschen Industrie-und Handelsunternehmen für Arzneimittel, Reformwaren und Körperpflegemittel e.V., Mannheim.

Polymeric dyes do not require any addition of an oxidizing agent to develop their dyeing effect.

This fact could possibly reduce the damage of the hair. In addition many of the perceived or documented disadvantages of current oxidative hair dyes like their skin irritation, skin sensibilization and allergenic properties can be prevented by the use of the inventive hair dyes.

Furthermore, the hair dyes according to the present invention are easier to apply and to use in formulations than oxidative hair dyes since no chemical reaction occurs upon application on the head. Especially advantageous is the fact, that the dyeing time is significantly shorter (ca. 5-10 min) than dyeing using oxidative dyes.

Furthermore, the polymeric dyes of the present invention may be combined with at least one cationic azo dye, for example the compounds disclosed in GB-A-2 319 776 as well as the oxazine dyes described in DE-A-299 12 327 and mixtures thereof with the other direct dyes mentioned therein.

The polymeric dyes of the present invention may also be combined with acid dyes, for example the dyes which are known from the international names (Color index), or trade names.

The polymeric dyes of the present invention may also be combined with uncharged dyes.

Furthermore, the polymeric dyes of the present invention may also be used in combination with oxidation dye systems.

Furthermore, autooxidizable compounds may be used in combination with the polymeric dyes of the present invention.

The polymeric dyes of the present invention may also be used in combination with naturally occurring dyes.

Furthermore, the polymeric dyes of the present invention may also be used in combination with capped diazotized compounds.

Suitable diazotized compounds are for example the compounds of formulae (1)-(4) in WO 2004/019897 (bridging gages 1 and 2) and the corresponding water-soluble coupling components (I)-(IV) as disclosed in the same reference on p. 3 to 5.

Furthermore, the dyes of the present invention can also be combined
 with dyes which are prepared by the reaction of a reactive carbonyl-compound and a CH-acidic compound as described in DE 10 2006 062 435 A1, WO 00038638, DE 10241076 and WO 05120445,
 with thiadiazol dyes as described in DE 10 2006 036898 and DE 10 2005 055496,
 with fluorescent stilbenic sulphur dyes as described in for example WO 07110532 and WO 07110542,
 with tetraazapentamethine dyes as described in WO 07071684 and WO 07071686,
 with dimeric cationic dyes as described in FR 2879195, FR 2879127, FR 2879190, FR 2879196, FR 2879197, FR 2879198, FR 2879199, FR 2879200, FR 2879928, FR 2879929 and WO 06063869,
 with azo and styryl dyes as described in EP 0850636, with polymeric anionic dyes as described in FR 2882929,
with disulfide dyes as described in WO 0597051, EP 1647580, WO 06136617,
with thiol dyes as described in WO 07025889, WO 07039527,
with conductive polymers as described in US 20050050650 and U.S. Pat. No. 7,217,295

The present invention also relates to formulations, which are used for the dyeing of organic materials, preferably keratin-containing fibers, and most preferably human hair, comprising at least one polymeric dye as defined in formula (1).

Preferably the polymeric dyes of the present invention are incorporated into the composition for treating organic material, preferably for dyeing in amounts of 0.001-5% by weight (hereinafter indicated merely by "%"), particularly 0.005-4%, more particularly 0.1-3%, based on the total weight of the composition.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, gel, or emulsion.

Customary the dyeing compositions are applied to the keratin-containing fiber in an amount of 50 to 100 g.

Preferred forms of formulations are ready-to-use compositions or multi-compartment dyeing devices or 'kits' or any of the multi-compartment packaging systems with compartments as described for example in U.S. Pat. No. 6,190,421, col 2, l. 16 to 31.

The pH value of the ready-to-use dyeing compositions is usually from 2 to 11, preferably from 5 to 10.

The dyeing compositions of the present invention are applied on the hair in a temperature range of 10 to 200, preferably 18 to 80, and most preferably from 20 to 40° C.

Suitable cosmetic hair-care formulations are hair-treatment preparations, e.g. hair-washing preparations in the form of shampoos and conditioners, hair-care preparations, e.g. pretreatment preparations or leave-on products such as sprays, creams, gels, lotions, mousses and oils, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or chamomile.

For use on human hair, the dyeing compositions of the present invention can usually be incorporated into an aqueous cosmetic carrier. Suitable aqueous cosmetic carriers include, for example W/O, O/W, O/W/O, W/O/W or PIT emulsions and all kinds of microemulsions, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially col 1, l. 70 to col 3, l. 55. The dyeing compositions according to the invention are also excellently suitable for the dyeing method described in DE-A-3 829 870 using a dyeing comb or a dyeing brush.

The constituents of the aqueous carrier are present in the dyeing compositions of the present invention in the customary amounts; for example emulsifiers may be present in the dyeing compositions in concentrations from 0.5 to 30% by weight and thickeners in concentrations from 0.1 to 25% by weight of the total dyeing composition.

Further carriers for dyeing compositions are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 243, l. 1 to p. 244, l. 12.

If the polymeric dyes of the present invention are used together with oxidation dyes and/or the addition salts thereof with an acid, they may be stored separately or together. Preferably the oxidation dyes and the direct dyes which are not stable to reduction or base are stored separately.

The polymeric dyes of the present invention may be stored in a liquid to paste-like preparation (aqueous or non-aqueous) or in the form of a dry powder.

When the dyes are stored separately, the reactive components are intimately mixed with one another directly before use. In the case of dry storage, a defined amount of hot (from 50 to 80° C.) water is usually added and a homogeneous mixture prepared before use.

The dyeing compositions according to the invention may comprise any active ingredients, additives or adjuvants known for such preparations, like surfactants, solvents, bases, acids, perfumes, polymeric adjuvants, thickeners and light stabilisers.

The following adjuvants are preferably used in the hair dyeing compositions of the present invention: non-ionic polymers, cationic polymers, acrylamide/dimethyldiallylammonium chloride copolymers, diethyl-sulfate-quaternized dimethylaminoethyl methacrylate/vinyl-pyrrolidone copolymers, vinylpyrrolidone/imidazolinium methochloride copolymers; -quaternized polyvinyl alcohol, zwitterionic and amphoteric polymers, anionic polymers, thickeners, structuring agents, hair-conditioning compounds, protein hydrolysates, perfume oils, dimethyl isosorbitol and cyclodextrins, solubilizers, anti-dandruff active ingredients, sub-stances for adjusting the pH value, panthenol, pantothenic acid, allantoin, pyrrolidone carboxylic acids and salts thereof, plant extracts and vitamins, cholesterol; -light stabilizers and UV absorbers, consistency regulators, fats and waxes, fatty alkanolamides, polyethylene glycols and polypropylene glycols having a molecular weight from 150 to 50 000, complexing agents, swelling and penetration substances, opacifiers, pearlising agents, propellants, antioxidants, sugar-containing polymers, quaternary ammonium salts and bacteria inhibiting agents.

The dyeing compositions according to the present invention generally comprise at least one surfactant. Suitable surfactants are zwitterionic or ampholytic, or more preferably anionic, non-ionic and/or cationic surfactants.

A further embodiment of the present invention relates to the dyeing of keratin-containing fibers.

The processes comprises
(a) treating the keratin-containing fiber with at least one polymeric dye of the present invention and
(b) leaving the fiber to stand and then rinsing the fiber.

The polymeric dyes according to the present invention are suitable for all-over dyeing of the hair, that is to say when dyeing the hair on a first occasion, and also for re-dyeing subsequently, or dyeing of locks or parts of the hair.

The polymeric dyes of the present invention are applied on the hair for example by massage with the hand, a comb, a brush, or a bottle, which is combined with a comb or a nozzle.

In the processes for dyeing according to the invention, whether or not dyeing is to be carried out in the presence of a further dye will depend upon the color shade to be obtained.

Further preferred is a process for dyeing keratin-containing fibers which comprises treating the keratin-containing fiber with at least one polymeric dye of the present invention, a base and an oxidizing agent.

A preferred embodiment for dyeing keratin-containing fibers, in particular human hair, with a polymeric dye of the present invention and an oxidizing agent, comprises $a_1$) treating the keratin-containing fiber with the oxidizing agent, which optionally contains at least one polymeric dye of the present invention, $b_1$) treating the keratin-containing fiber with an oxidizing agent free composition, which optionally contains at least one polymeric dye of the present invention; or alternatively $a_2$) treating the keratin-containing fiber with an oxidizing agent free composition, which optionally contains at least one polymeric dye of the present invention;

$b_2$) treating the keratin-containing fiber with an oxidizing agent, which optionally contains least one polymeric dye of the present invention;

with the proviso that at least in one of the process steps $a_1$), $a_2$), $b_1$) or $b_2$) at least one polymeric dye of the present invention is present.

In general, the oxidizing agent containing composition is left on the fiber for 0 to 45 minutes, in particular for 15 to 30 minutes at 15 to 45° C.

The oxidizing agent free composition usually comprises customary adjuvants and additives.

In general, the polymeric dyes of the present invention and the oxidizing agent free composition are left on the fiber for 5 to 45 minutes, in particular for 10 to 25 minutes at 15 to 50° C.

One preferred embodiment of this process is to wash the hair after dyeing with a shampoo and/or a weak acid, such as citric acid or tartrate acid.

The polymeric dyes according to the present invention which are stable to reduction can be stored together with the oxidizing agent free compositions and may be applied as a single composition.

Advantageously the compositions comprising a polymeric dye of the present invention which are not stable to reduction are prepared with the oxidizing agent free composition just before the dyeing process.

In a further embodiment, the polymeric dye of the present invention and the oxidizing agent free composition may be applied simultaneously or in succession.

Customary, the oxidizing agent containing composition is evenly applied in a sufficient amount related to the amount of hair, usually in amounts of 30 to 200 g.

Oxidizing agents are for example persulfate or dilute hydrogen peroxide solutions, hydrogen peroxide emulsions or hydrogen peroxide gels, alkali. earth metal peroxides, organic peroxides, such as urea peroxides, melamine peroxides, or alkalimetalbromate fixations are also applicable if a shading powder on the basis of semi-permanent, direct hair dyes is used.

Further preferred oxidizing agents are oxidizing agents to achieve lightened coloration, as described in WO 97/20545, especially p. 9, I. 5 to 9, oxidizing agents in the form of permanent-wave fixing solution, as described in DE-A-19 713 698, especially p. 4, I. 52 to 55, and I. 60 and 61 or EP-A-1062940, especially p. 6, I. 41 to 47 (and in the equivalent WO 99/40895).

Most preferred oxidizing agent is hydrogen peroxide, preferably used in a concentration from about 2 to 30%, more preferably about 3 to 20% by, and most preferably from 6 to 12% by weight the corresponding composition.

The oxidizing agents may be present in the dyeing compositions according to the invention preferably in an amount from 0.01% to 6%, especially from 0.01% to 3%, based on the total dyeing composition.

In general, the dyeing with an oxidative agent is carried out in the presence of a base, for example ammonia, alkali metal carbonates, earth metal (potassium or lithium) carbonates, alkanol amines, such as mono-, di- or triethanolamine, alkali metal (sodium) hydroxides, earth metal hydroxides or compounds of the formula

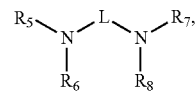

wherein
L is a propylene residue, which may be substituted with OH or $C_1$-$C_4$alkyl; and
$R_5$, $R_6$, $R_7$ and $R_8$ independently or dependently from each other are hydrogen; $C_1$-$C_4$alkyl; or hydroxy-($C_1$-$C_4$)alkyl.

The pH-value of the oxidizing agent containing composition is usually about 2 to 7, and in particular about 2 to 5.

One preferred method of applying formulations-comprising the polymeric dyes according to the present invention on the keratin-containing fiber, preferably the hair is by using a multi-compartment dyeing device or "kit" or any other multi-compartment packaging system, as described for example in WO 97/20545 on p. 4, I. 19 to I. 27.

Generally the hair is rinsed after treatment with the dyeing solution and/or permanent-wave solution.

A further preferred embodiment of the present invention relates to a method of dyeing keratin-containing fibers with oxidative dyes, which comprises a. mixing at least one polymeric dye of the present invention and optionally at least one coupler compound and at least one developer compound, and an oxidizing agent, which optionally contains at least one further dye, and b. contacting the keratin-containing fibers with the mixture as prepared in step a.

For adjusting the pH-value organic or inorganic acids, as for example described in DE 199 59 479, col 3, I. 46 to I. 53 are suitable.

Furthermore, the present invention relates to a process of dyeing keratin-containing fibers with the polymeric dyes according to the present invention and autooxidable compounds and optionally further dyes.

The process comprises a. mixing at least one autooxidable compound and at least one developer compound and at least one polymeric dye according to the present invention and optionally further dyes, and b. treating the keratin-containing fiber with the mixture prepared in step a.

Furthermore, the present invention relates to a process for dyeing keratin-containing fibers with the polymeric dyes of the present invention and capped diazotized compounds, which comprises, a. treating the keratin-containing fibers under alkaline conditions with at least one capped diazotized compound and a coupler compound, and optionally a developer compound and optionally an oxidizing agent, and optionally in the presence of a further dye, and optionally with at least one polymeric dye of the present invention, and b. adjusting the pH in the range of 6 to 2 by treatment with an acid, optionally in the presence of a further dye, and optionally at least one polymeric dye of the present invention with the proviso that at least in one step a. or b. at least one polymeric dye of the present invention is present.

The capped diazotized compound and coupler compound and optionally the oxidizing agent and developer compound can be applied in any desired order successively or simultaneously.

Preferably, the capped diazotized compound and the coupler compound are applied simultaneously, in a single composition.

"Alkaline conditions" denotes a pH in the range from 8 to 10, preferably 9-10, especially 9.5-10, which are achieved by the addition of bases, for example sodium carbonate, ammonia or sodium hydroxide.

The bases may be added to the hair, to the dye precursors, the capped diazotized compound and/or the water-soluble coupling component, or to the dyeing compositions comprising the dye precursors.

Acids are for example tartaric acid or citric acid, a citric acid gel, a suitable buffer solution with optionally an acid dye.

The ratio of the amount of alkaline dyeing composition applied in the first stage to that of acid dyeing composition applied in the second stage is preferably about from 1:3 to 3:1, especially about 1:1.

The alkaline dyeing compositions of step a. and the acid dyeing compositions of step b. are left on the fiber for 5 to 60 minutes at 15 to 45° C., in particular for 5 to 45 minutes at 20 to 30° C.

Furthermore, the present invention relates to a process for dyeing keratin-containing fibers with the polymeric dyes of the present invention and at least one acid dye.

The following examples serve to illustrate the preparation of the polymeric hair dyes according to the present invention and the corresponding processes for hair dyeing without limiting the processes thereto. Unless specified otherwise, parts and percentages relate to weight. The amounts of dye specified are relative to the material being dyed.

A. PREPARATION EXAMPLES

The examples A1 to A5 are prepared by reacting an aqueous solution of Tinofix Cl® (Ciba Inc.) containing 33% of active with one of the dyes Dye 1 to 3. The reaction conditions for each example are given in Table 1. The reactions are followed by TLC. The reaction mixtures are used for coloration without further treatment.

| | Formula | Disclosed in |
|---|---|---|
| Dye 1 | Cl⁻ (structure) | WO 2004/7083312 |
| Dye 2 | MeSO₄⁻ (structure) | IP.com Journal (2004), 4(9), 31 |
| Dye 3 | MeSO₄⁻ (structure) | GB 2412916 |

TABLE 1

| Example | Dye | Quantity Tinofix Cl 33% active | Quantity Dye | T (°C) | Time | Product color |
|---|---|---|---|---|---|---|
| A1 | 2 | 2 ml | 0.4 mmol | 20 | 20 days | Red |
| A2 | 1 | 5 ml | 1 mmol | 20 | 20 days | Red |
| A3 | 3 | 2 ml | 0.4 mmol | 20 | 20 days | Violet |
| A4 | 2 | 1 ml | 1 mmol | 60 | 7 days | Red |
| A5 | 3 | 1 ml | 1 mmol | 60 | 7 days | violet |

B. APPLICATION EXAMPLES

Hair Samples

For the application examples the following hair types have been used:
1 blonde hair tress (VIRGIN White Hair fro IMHAIR Ltd., via G. Verga 8, 90134 Palermo (Italy)),
1 middle blonde hair tress (UNA-Europ. nature hair, Color middle blonde from Fischbach & Miller, Postfach 1163, 88461 Laupheim, Germany),
1 bleached hair tress (UNA-Europ. nature hair, Color white bleached blonde from Fischbach & Miller, Postfach 1163, 88461 Laupheim, Germany).

Coloring Solution:
0.2 or 1% w/w of one of the dyes described in examples A1 to A5 are dissolved in a Plantaren solution (10% w/w Plantacare 200UP (ID: 185971.5) in water; pH adjusted to 9.5 with 50% citric acid solution or monoethanolamine solution).

The hair tresses are dyed according to the following procedure:

The coloring solution is applied directly to the dry hair, incubated for 20 min. at room temperature, and then rinsed off under tap water (water temperature: 37° C.+/−1° C.; flow rate of water: 5-6 l/min.). Then it is pressed out with a paper towel and dried over night at room temperature on a glass plate.

For the determination of the wash fastness two sets of hair tresses are dyed under the same conditions. One set of the dyed tresses is washed with a commercial shampoo (GOLDWELL definition Color & Highlights, color-conditioner shampoo) using approx. 0.5 g shampoo for each tress under tap water (water temperature: 37° C.+/−1° C.; flow rate 5-6 l/min). Finally the tresses are rinsed under tap water, pressed out with a paper towel, combed and dried with a hair dryer or at room temperature. This procedure is repeated 10 times.

Then the color loss of the set of washed tresses relative to the set of unwashed tresses is evaluated using the Grey Scale (from 1 to 5 with 5 being completely unchanged) according to: Industrial Organic Pigments by Herbst&Hunger, 2$^{nd}$ ed., p. 61, Nr 10: DIN 54 001-8-1982, "Herstellung and Bewertung der Änderung der Farbe", ISO 105-A02-1993.

TABLE 2

| Example | Dye | concentration | Hair Type | Color | Intensity | Brilliance | Wash-fastness Grey scale |
|---|---|---|---|---|---|---|---|
| B1 | A1 | 0.2% | blond | red | moderate | good | 4 |
|  |  |  | middle blond | red | moderate | good | 4 |
|  |  |  | bleached | red | moderate | good | 3-4 |
| B2 | A1 | 1 | blond | red | good | good | 4-5 |
|  |  |  | middle blond | red | good | good | 4 |
|  |  |  | Bleached | red | good | good | 4 |
| B3 | A2 | 0.2 | Blond | red | moderate | good | 4 |
|  |  |  | middle blond | red | moderate | good | 4-5 |
|  |  |  | Bleached | red | moderate | good | 3-4 |
| B4 | A2 | 1 | Blond | red | good | good | 4 |
|  |  |  | middle blond | red | good | good | 4-5 |
|  |  |  | Bleached | red | good | good | 3-4 |
| B5 | A3 | 0.2 | Blond | violet | moderate | Bad | 3 |
|  |  |  | middle blond | violet | moderate | Bad | 4 |
|  |  |  | Bleached | violet | moderate | bad | 3 |
| B6 | A3 | 1 | Blond | violet | good | moderate | 4-5 |
|  |  |  | middle blond | violet | good | moderate | 4 |
|  |  |  | Bleached | violet | good | moderate | 3-4 |
| B7 | A4 | 0.2 | blond | red | good | good | 3 |
|  |  |  | middle blond | red | good | good | 3 |
|  |  |  | bleached | red | good | good | 3 |
| B8 | A4 | 1 | blond | red | good | good | 4-5 |
|  |  |  | middle blond | red | good | good | 4 |
|  |  |  | bleached | red | good | good | 4 |
| B9 | A5 | 0.2 | blond | red | good | moderate | 3 |
|  |  |  | middle blond | red | good | moderate | 3-4 |
|  |  |  | bleached | red | good | moderate | 3 |
| B10 | A5 | 1 | blond | red | good | good | 2-3 |
|  |  |  | middle blond | red | good | good | 3 |
|  |  |  | bleached | red | good | good | 2-3 |

The invention claimed is:

1. Polymeric dye obtained by the reaction of
(a) a basic polycondensate with
(b) an electrophilic dye of formula
(2) P—X—Y$^{a+}$ An$^{a-}$; wherein
the basic polycondensate (a) is obtained by the reaction of
(a$_1$) an amine of formula

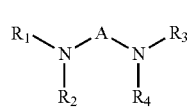

(1)

in the presence of an anhydrous solvent with an ammonium salt
(a$_2$) with a cyanamide;
wherein
R$_1$, R$_2$, R$_3$ and R$_4$ independently from each other are hydrogen; or C$_1$-C$_4$alkyl, which may be substituted by amino, hydroxy, cyano or C$_1$-C$_4$alkoxy;

A is C$_2$-C$_{20}$alkylene, which may be substituted or interrupted by one or more than one hetero atoms;
P is a reactive grouping capable of reacting with a nitrogen nucleophile;
X is a linkage group selected from C$_1$-C$_{30}$alkylene, C$_2$-C$_{12}$alkenylene, C$_5$-C$_{10}$arylene, C$_5$-C$_{10}$cycloalkylene and C$_1$-C$_{10}$alkylene(C$_5$-C$_{10}$arylene) which may be interrupted and/or terminated at one or both ends by one or more than one —O—, —S—, —N=, —N(R$_5$)—, —S(O)—, SO$_2$, —(CH$_2$CH$_2$—O)$_{1-5}$—, —(CH$_2$CH$_2$CH$_2$—O)$_{1-5}$—, —C(O)—, —C(O)O—, —OC(O)—,

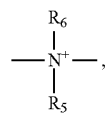

—CON(R$_5$)—, —C(NR$_5$R$_6$)$_2$—, —(R$_5$)NC(O)—, —C(S)R$_5$— or an optionally substituted, saturated or unsaturated, fused or non-fused aromatic or nonaromatic (hetero)cyclic bivalent radical optionally comprising at least one heteroatom; —O—; —S—; —N(R$_5$)—; —S(O)—; —SO$_2$—; —(CH$_2$CH$_2$—O)$_{1-5}$—; —C(O)—; —C(O)O—, —OC(O)—;

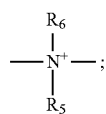

—CON($R_5$)—; —$SO_2$N($R_5$)—; —C(N$R_5R_6$)$_2$—; —($R_5$)NC(O)—; —C(S)$R_5$—; saturated or unsaturated, fused or non-fused aromatic or nonaromatic bivalent radical optionally comprising at least one heteroatom; which is optionally substituted by $C_1$-$C_{30}$alkyl, $C_1$-$C_{30}$alkoxy, $C_2$-$C_{12}$alkenyl, $C_5$-$C_{10}$aryl, $C_5$-$C_{10}$cycloalkyl, $C_1$-$C_{10}$alkyl($C_5$-$C_{10}$arylene), halogen or hydroxy; or the direct bond;

Y is a residue of an organic dye;

$R_5$ and $R_6$ independently from each other are hydrogen; unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl);

a is 1, 2 or 3; and

An is an anion.

2. Dye according to claim 1, wherein

X is a bivalent radical of formula (1a) -(T)$_t$(Z)$_z$—, wherein

T is a radical selected from saturated or unsaturated, linear or branched —$C_1$-$C_{12}$alkylene, —C(O)—, —(CH$_2$CH$_2$—O)$_{1-5}$-, —(CH$_2$CH$_2$CH$_2$—O)$_{1-5}$-, —C(O)O—, —OC(O)—, —N($R_5$)—, —CON($R_5$)—, —($R_5$)NC(O)—, —O—, —S—, —S(O)—, —S(O)$_2$—, —S(O)$_2$N($R_5$)— and —N$^+$($R_5$)($R_6$)—, which may be interrupted and/or terminated at one or both ends by one or more than one —O—, —S—, —N($R_5$)—, —C(O)—,

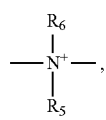

—CON($R_5$)—, —($R_5$)NC(O)— and which is optionally substituted by $C_1$-$C_6$alkyl, $C_1$-$C_6$alkoxy, $C_6$-$C_{10}$aryl, halogen or hydroxy;

Z is —(CH$_2$)$_2$SO$_2$—; —CH$_2$—CHR$_6$—CO—NR$_5$—; or a biradical of formula

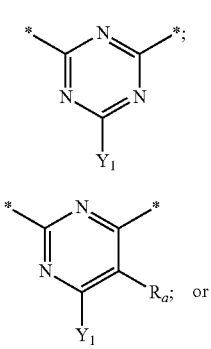

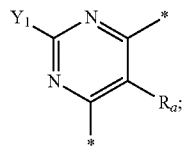

$R_5$ and $R_6$ independently from each other are hydrogen; $C_1$-$C_6$alkyl; $C_1$-$C_6$-alkoxy; $C_1$-$C_6$-alkylamino; $C_6$-$C_{10}$aryloxy; or $C_6$-$C_{10}$arylamino;

$R_a$ is hydrogen; $C_1$-$C_6$alkyl; $C_1$-$C_6$-alkoxy; $C_1$-$C_6$-alkylamino; $C_6$-$C_{10}$-aryloxy; $C_6$-$C_{10}$-arylamino; SO$_2R_5$; chlorine; or fluorine;

$Y_1$ is $R_a$; or the residue of an organic dye;

a is 1, 2 or 3; and t and z, independently from each other are 0; or 1.

3. Dye according to claim 1, wherein

Y is selected from the group of anthraquinone, acridine, azo, azamethine, hydrazomethine, triphenylmethane, benzodifuranone, coumarine, diketopyrrolopyrrol, dioxazine, diphenylmethane, formazane, indigoid indophenol, naphthalimide, naphthoquinone, nitroaryl, merocyanine, methine oxazine, perinone, perylene, pyrenequinone, phtalocyanine, phenazine, quinoneimine, quinacridone, quinophtalone, styryl, stilbene, xanthene, thiazine and thioxanthene dyes.

4. Dye according to claim 1, wherein

Y is selected from anthraquinone, azo, azamethine, hydrazomethine, merocyanine, methine and styryl dyes.

5. Dye according to claim 1, wherein

P is selected from a halogen; tosylate; mesylate; sulfonylchloride; acid chloride; and another reactive grouping selected from an epoxide; and a Michael system selected from an α-β unsaturated carbonyl and a sulfonyl system.

6. Dye according to any of claim 1, wherein the molecular weight of the polymeric dye is from 400 to 50000.

7. Dye according to claim 1, wherein

A is $C_1$-$C_{20}$alkylene.

8. Dye according to claim 1, wherein the compound of formula (1) is a polyethylenepolyamine.

9. Dye according to claim 1, wherein the compound of formula (1) is diethylenetriamine or hexamethylene-1,6-diamine.

10. Dye according to claim 1, wherein the cyanamide used in step (a$_2$) is dicyandiamide or dicyanamide.

11. A cosmetic composition comprising at least one polymeric dye as defined in claim 1.

12. A composition according to claim 11 comprising in addition at least one single further direct dye and/or an oxidative agent.

13. A composition according to claim 11 in form of a shampoo, a conditioner, a gel or an emulsion.

14. A method of dyeing organic material, which comprises treating the organic material with at least one dye as defined in claim 1.

15. A method according to claims 14, wherein the dye further comprises an oxidative agent and, optionally, a further direct dye.

16. A method according to claim 14 wherein the dye further comprises at least one single oxidative dye, or at least one single oxidative dye and an oxidative agent.

17. A method according to claim 14, wherein the organic material is selected from keratin-containing fibers.

18. A method according to claim 17 wherein the keratin-containing fiber is human hair.

* * * * *